US010209195B2

(12) United States Patent
Jian

(10) Patent No.: US 10,209,195 B2
(45) Date of Patent: Feb. 19, 2019

(54) DEVICE FOR COLLECTING SURFACE-ENHANCED RAMAN SCATTERING SPECTRUM USING FULL-APERTURE-ANGLE PARABOLIC MIRROR

(71) Applicant: Peirong Jian, Liaoning (CN)

(72) Inventor: Peirong Jian, Liaoning (CN)

( * ) Notice: Subject to any disclaimer, the term of this patent is extended or adjusted under 35 U.S.C. 154(b) by 0 days.

(21) Appl. No.: 15/925,094

(22) Filed: Mar. 19, 2018

(65) Prior Publication Data

US 2018/0209909 A1 Jul. 26, 2018

Related U.S. Application Data

(63) Continuation-in-part of application No. PCT/CN2016/099208, filed on Sep. 18, 2016.

(30) Foreign Application Priority Data

Sep. 20, 2015 (CN) .......................... 2015 1 0615037

(51) Int. Cl.
*G01J 3/44* (2006.01)
*G01N 21/65* (2006.01)
*A61B 5/00* (2006.01)
*G02B 5/10* (2006.01)

(52) U.S. Cl.
CPC ......... *G01N 21/658* (2013.01); *A61B 5/0075* (2013.01); *G01J 3/44* (2013.01); *G01N 21/65* (2013.01); *G02B 5/10* (2013.01)

(58) Field of Classification Search
CPC ................. G01N 21/65; G01N 21/658; G01N 2021/656; G01J 3/44; G01J 3/02

USPC .......................................................... 356/301
See application file for complete search history.

(56) References Cited

U.S. PATENT DOCUMENTS

| 5,122,127 A | 6/1992 | Stanley |
| 2011/0081110 A1 | 4/2011 | Sullivan et al. |

FOREIGN PATENT DOCUMENTS

| CN | 101794961 B | 7/2011 |
| CN | 202104921 U | 1/2012 |
| CN | 102721679 A | 10/2012 |
| CN | 103499562 A | 1/2014 |

*Primary Examiner* — Md M Rahman
(74) *Attorney, Agent, or Firm* — Novick, Kim & Lee, PLLC; Allen Xue

(57) ABSTRACT

A device for collecting surface-enhanced Raman scattering spectra using a full-aperture-angle parabolic mirror. The device is a small-sized ultra-sensitive SERS Raman spectroscopic enhanced probe and a spectrometer, a surface plasmon resonance (SPR) Raman spectroscopic probe and a spectrometer, a spectrum analyzer having triple functions of an SPR Raman/absorption dual-spectrum and refractive index, a flow particle Raman analysis/micro-fluidic Raman analysis probe and a spectrometer, a minimally invasive flexible lumen Raman spectroscopic probe and a spectrometer and a Raman intelligent surgical scalpel. An external reflective or internal reflective parabolic mirror at full aperture angle is adopted to collect Raman scattering systems and SERS substrates to ensure ultra-high sensitivity. A portable and hand-held Raman spectrometer would be widely applied to various trace analysis such as food safety and early-stage cancer screening, environmental safety screening and detection.

12 Claims, 8 Drawing Sheets

DEVICE FOR COLLECTING SURFACE-ENHANCED RAMAN SCATTERING SPECTRUM USING FULL-APERTURE-ANGLE PARABOLIC MIRROR

TECHNICAL FIELD

The present disclosure provides an apparatus for collecting surface-enhanced Raman scattering spectrum with a full aperture angle parabolic mirror, and belongs to the field of spectrum analysis.

BACKGROUND

In the international market, there are many well-established large-scale micro-Raman spectrometer used for research, all of which are designed with conventional optical elements and large structures of more than one meter in length. The use of surface-enhanced Raman scattering (SERS)substrates allows for ultra-high-sensitivity SERS-micro-Raman spectroscopy testing function. Such a device has high sensitivity, good performance, high cost, and large size but cannot be widely and portably used.

In addition, in the international market, although there are many models of portable small Raman spectrometers, which usually use fiber Raman probe disclosed in U.S. Pat. No. 5,122,127. The optical fiber Raman probe has a numerical aperture NA of 0.25, which is corresponding to a small collecting aperture angle Ω, where Ω is about 0.25sr, and the sensitivity is applicable to only analysis of samples with higher abundance and higher concentration, leading to restriction on popularization and application. There is urgent demand on upgrading and developing portable probes and small Raman spectrometers with ultra-high sensitivity.

At present, due to that: the poor coherence of the semiconductor laser beams used by many optical fiber Raman probes to excite samples, the coherence of the beams for sample excitation is destroyed via multimode optical fiber transmission, some compact Raman probes and spectrometers using objective NA smaller even with aspherical objective NA≈0.5 to focus the laser beam to excite the sample, the quality of the objective and the laser beam do not meet the requirements and other factors, make it difficult to effectively use the SERS substrate to achieve ultra-high sensitivity.

At the present stage, with the condition of the existing lasers and Charge Coupled Device (CCD) photo-detectors, to obtain SERS high enhancement, there are the following three most basic requirements: the need to ensure that the laser beam for exciting the samples has a good coherence; appropriate focus spot; and optical systems on the order of 2-10 microns and collecting Raman scattering with large aperture angles. However, all the current portable small Raman probes and spectrometers cannot simultaneously meet the three basic requirements of high-sensitivity SERS. Therefore, Raman spectroscopy has low detection sensitivity and cannot be applied to trace analysis on ultra-low concentration samples.

SUMMARY

Technical Problem

In order to solve the above technical problem, the present disclosure provides a device for collecting surface enhanced Raman spectrum with a full aperture angle parabolic mirror of near $2\pi$ or $4\pi$sr, and design of excited optical path with ingeniously coordination.

Technical Solution

The technical solution of the present disclosure is as follows. There is provided a device for collecting surface-enhanced Raman spectrum by a full aperture angle parabolic mirror. The device may be a SERS probe and spectrometer, a surface plasmon resonance (SPR) Raman spectroscopy probe and spectrometer, a SPR Raman/absorption dual spectrum and refractive index three-function probe and spectroscopic analyzer, a flow particle Raman/micro-fluidic Raman analyzing probe and spectrometer, a minimal invasive flexible endoluminal Raman spectroscopy probe and spectrometer, and surgery Raman smart surgical knife; an enhanced Raman spectroscopy probe in each of the above six devices is equipped with a compact $TEM_{00}$ single longitudinal mode laser with good coherence and a compact spectrometer, the $TEM_{00}$ single longitudinal mode laser using single-mode fiber and the compact spectrometer using multi-mode fiber; the compact $TEM_{00}$ single longitudinal mode laser and the compact spectrometer are connected to the Raman spectroscopy probe via transmission of an optical fiber, or the laser and the compact spectrometer as well as an optical path of the Raman spectroscopy probe are designed as an integrated compact Raman spectrometer, wherein the full aperture angle of the device for collecting surface enhanced Raman spectrum is 1.5-2πsr or 3.5-4πsr.

(1) The SERS probe and spectrometer comprises a single mode optical fiber connector or laser 1, a first lens 2, a 45-degree incident long pass bichromal filter 3, a SERS substrate+sample 5, a slide 6, an external reflection parabolic mirror 7-1 equipped with a coaxial confocal built-in microscope objective lens 4-1, an internal reflection parabolic mirror 7-2 equipped with a coaxial confocal external microscope objective lens 4-2, an aspherical large aperture objective lens 8, a small space filter pinhole 9, a small aperture lens 10, a vertically incident long pass bichromal filter 11, a total internal reflection prism or mirror, 45-degree short pass bichromal filter 12, a second lens 13 and a optical fiber connector or a compact spectrometer 14;

Wherein in the SERS probe and spectrometer comprises a single mode optical fiber connector or laser 1, a first lens 2, a 45-degree incident long pass bichromal filter 3, a SERS substrate+sample 5, a slide 6, an external reflection parabolic mirror 7-1 equipped with a coaxial confocal built-in microscope objective lens 4-1, an internal reflection parabolic mirror 7-2 equipped with a coaxial confocal external microscope objective lens 4-2, an aspherical large aperture objective lens 8, a small space filter pinhole 9, a small aperture lens 10, a vertically incident long pass bichromal filter 11, a total internal reflection prism or mirror, 45-degree short pass bichromal filter 12, a second lens 13 and a optical fiber connector or a compact spectrometer 14;

wherein through the single-mode optical fiber connector or laser 1, a laser beam with good coherence is converted into a parallel excitation laser beam by the first lens 2, and passes through a 45-degree incident long pass bichromal filter 3 provided on a main optical axis; then the optical path is branched into two kinds of structures, i.e., a structure using the external reflection parabolic mirror 7-1 and the other is a structure using the internal reflection parabolic mirror 7-2, wherein in the structure using the external reflection parabolic mirror, the excitation laser beam passes through the built-in microscope objective lens 4-1, and in the, other structure using the internal reflection parabolic mirror, the excitation laser beam passes through the external microscope objective lens 4-2; the excitation laser beams for the two structures are both focused onto the SERS substrate+sample 5 provided on the slide 6, and the SERS Raman scattering beam in about $2\pi$ solid angle as backscattered by the sample passed through the two structures objectives and reflected by parabolic mirrors, and is collected and synthesized into a large aperture parallel beam, the large aperture parallel beam is focused by the aspherical surface large aperture lens 8, is isolated from stray light via the small space filtering pinhole 9, is converted into a small aperture parallel beam by the small aperture lens 10 and is isolated from Rayleigh scattering by the long pass bichromal filter 11, the main optical axis is deflected by 90 degrees by the total internal reflection prism or mirror or 45-degree incident short pass bichromal filter 12, and the small aperture parallel beam is isolated from Rayleigh scattering and stray light by the long pass bichromal filter 11, and Raman beam is focused onto the optical fiber connector by the second lens 13 and is coupled onto an incident slit of a compact optical fiber spectrometer by a multi-mode optical fiber to construct a compact SERS probe, or the focal spot of the Raman beam is adjusted directly onto a slit of a compact spectrometer to construct a compact SERS spectrometer;

wherein the intercept of the external reflection parabolic mirror 7-1 and the internal reflection parabolic mirror 7-2, both truncated at the focal point, the intercept b is about 4 to 10 mm, and the parallel output backscattered Raman scattering beam collected by the reflection of each mirror is a hollow parallel beam, in the hollow blind zone specially designed and provided with the built-in microscope objective 4-1, with a long working distance and a numerical aperture NA=0.4-0.5 for external reflection parabolic mirror 7-1, and for the internal reflection parabolic mirror 7-2 provided with an external microscope objective lens 4-2 with NA of 0.25, on the one hand to ensure good coherence of the excitation beam and spot size of 2-10 µm focused on the sample, so that SERS of sample has ultra-high enhancement factor; on the other hand to use the built-in microscope objective lens 4-1 and the external microscope objective 4-2 such that Raman beams in the reflection blind zone of the external reflection parabolic mirror 7-1 and the internal reflection parabolic mirror 7-2 are collected, so that a total effective full aperture angle of backscattered Raman scattering beam achieved of 1.8-2$\pi$sr.

(2) In the device for collecting surface enhanced Raman scattering spectrum with a full aperture angle parabolic mirror, wherein in the SERS probe and spectrometer, two systems of reflection parabolic mirror, i.e., a system using an external reflection parabolic mirror or a system using an internal reflection parabolic mirror are used, a SPR plug-in system is additionally provided for detecting SPR Raman spectrum to construct a SPR Raman spectroscopy probe and spectrometer, the plug-in system comprises a laser 1, a build-in microscope objective 4-1 corresponding to an external reflection parabolic mirror 7-1, or an external microscope objective 4-2 corresponding to an internal reflection parabolic mirror 7-2, a third lens 15, a linear straight-line trimmer 16, a right-angle prism 17, the fourth lens 18, a photo-detector 19 and a hemispherical glass sample stage 20; an excitation beam generated by the laser 1 is narrowed by the third lens 15 to reduce the diameter of the excitation beam to 1-2 mm thin laser beam, the thin laser beam is deflected by a right-angle prism 17 with a thickness of 3-4 mm to be parallel to the main optical axis and then reflected by the external reflection parabolic mirror 7-1 or the internal reflection parabolic mirror 7-2 to be focused on a focus of the corresponding parabolic mirror, wherein in case of the external reflection parabolic mirror 7-1, a hemispherical quartz glass sample stage 20 is provided; the laser beam totally internally reflected by the SERS substrate+sample 5 is reflected by the external reflection parabolic mirror 7-1 or the internal reflection parabolic mirror 7-2 and deflected onto a fourth lens 18 by a second right-angle prism 17 with a thickness of 3-4 mm and then directly enters the photo-detector system 19; the 'laser 1+the third lens 15' is adjusted by the linear micrometer 16 to finely displaced in a direction parallel to the main optical axis, that is, an incident angle of an excitation beam with respect to the 'SERS substrate+sample 5' is adjusted; the incident angle is adjusted to the SPR incident angle $\theta_{SPR}$ such that the excitation beam is coupled to and resonates with the SPR of 'SERS substrate+sample 5'; while adjusting the incident angle of the excitation laser beam by the linear micrometer 16, the intensity of the SPR reflected beam is read and detected by the photo-detector 19, and when the photo-detector 19 shows a minimum value, the incident angle reaches the SPR-$\theta_{SPR}$; at this time, the detected Raman spectrum is the SPR Raman spectrum of the sample; and an unknown refractive index n of the sample is detected according to readings of the linear micrometer 16 and a standard curve n-$\theta_{SPR}$ calibrated using a refractive index of a known sample, such as pure water and other pure liquids.

In the device for collecting surface enhanced Raman scattering spectrum with a full aperture angle parabolic mirror, for the SPR plug-in system, wherein instead of the linear micrometer 16 which adjusts the position of 'the laser 1+the third lens 15', a precise optical flat glass is inserted into a parallel thin laser beam generated by the laser 1 in a SPR Raman spectroscopy probe and spectrometer, the optical flat glass is fixed on stage with a precise electric control detecting angular displacement to control and measure a rotary angle of the optical flat glass, and the rotary angle of the optical flat glass adjusts translational movement of the parallel thin laser beam, such that an incidence angle $\theta_{SPR}$ of the excitation beam with respect to SERS substrate+sample 5 is adjusted.

(3) In the device for collecting surface enhanced Raman scattering spectrum with a full aperture angle parabolic mirror, wherein a plug-in system for detecting absorption spectrum of a sample is added to the SPR Raman spectroscopy probe and spectrometer, and the plug-in system comprises an assembly of 'a wide-spectrum white light source 21 and a fifth lens 13+optical fiber spectrometer 22' to construct a SPR Raman/absorption dual spectrums and refractive index three-function Raman probe and spectrometer; the plug-in system for detecting SPR Raman spectrum is adjusted to make the incident angle of the excitation beam to locate at SPR-$\theta_{SPR}$, SPR-Raman spectrum detection and refractive index detection of the SERS substrate+sample 5 are performed; then, a switching to the plug-in system assembly for detecting absorption spectrum of the sample is performed: the laser 1 for exciting the SPR Raman spectrum is replaced with the wide-spectrum white light source 21, an assembly of 'a fourth lens 18+a photo-detector 19' is replaced with an assembly of 'a fifth lens 13+an optical fiber spectrometer 22' to detect the absorption spectrum of the same sample, to achieve the SPR Raman/absorption dual spectrums and refractive index three-function spectrum analysis of the sample; wherein on the truncated parabolic mirror is installed with or without a hemisphere mirror 23, on hemisphere surface having plated the short pass bichromal filter film, the center of hemisphere mirror 23 is homocentric with respect to a focal point of the parabolic mirror, and the aperture angle of the Raman optical system for collecting the Raman scattered beam is about 3.5-4πsr or 1.8-2πsr.

(4) The device for collecting the surface enhanced Raman scattering spectrum with a full aperture angle parabolic mirror is designed as a flow particle Raman analysis/micro-fluidic Raman analysis probe and spectrometer, comprising a 'back' scattering type and a 'back+forward' scattering type two types of flow particle Raman analysis/micro-fluidic Raman probe and spectrometer, is divided into non-truncated monolithic internal parabolic mirror system and focal plane F-F truncated external reflection parabolic mirror system; a monolithic internal parabolic mirror system, wherein a hole or groove d-d matching an outer diameter of a capillary sample cell extends from a top to a focus of the internal parabolic mirror, the hole being perpendicular to the main optical axis; and a focal plane F-F truncated external reflection parabolic mirror system, wherein a mirror 23 with a hemisphere surface having plated thereon a short pass bichromal filtering film is provided on a focus plane of the external reflection parabolic mirror, a spheroid center of the mirror is overlapped with a focal point of the external reflection parabolic mirror;

the focal plane F-F truncated external reflection parabolic mirror system is applied to a near UV excitation Raman spectroscopy system, the whole system uses reflective components and quartz transmission components; thin parallel near ultraviolet laser beam emitted by an near ultraviolet laser 1 is reflected by a 45-degree mirror and is reflected by an external reflection parabolic mirror 7-1 and focused onto a capillary Raman sample cell 24, axis of which passes through a focus of the parabolic mirror; an intercept b of the parabolic mirror is 3-6 mm, and an effective aperture angle of the system of 'hemispherical mirror+the external reflection parabolic mirror' for collecting Raman scattering beam is 3.5-4πsr.

(5) In the device for collecting the surface enhanced Raman scattering spectrum with a full aperture angle parabolic mirror, the SERS probe and spectrometer is designed as a hand-held SPR Raman spectrometer and comprises a laser 1, an external reflection parabolic mirror 7-1 or an internal reflection parabolic mirror 7-2, a small space filtering pinhole 9, an incident 45-degree long pass bichromal filter 25, an incident 45-degree short pass bichromal filter 26, a sixth lens 27, a seventh lens 28, an eighth lens 29 and a micro-spectrometer; the hand-held SPR Raman spectrometer is divided into two types, i.e., a type of a truncated parabolic mirror and a type of a whole parabolic mirror, an intercept of the parabolic mirror 3<b<0.2 mm, a hole or groove d-d perpendicular to the main optical axis extends from a top to a focus of the whole parabolic mirror and is configured to receive the capillary sample cell or microchannel Raman chip, an effective aperture angle of the Raman optical system for collecting Raman scattering is 3.5-4πsr.

(6) The device for collecting the surface enhanced Raman scattering spectrum with a full aperture angle parabolic mirror may also be designed as a minimal invasive flexible endoluminal Raman spectroscopy probe and spectrometer, the minimal invasive flexible endoluminal Raman spectroscopy probe and spectrometer uses a flexible optical fiber to connect the probe to a laser and the spectrometer, and comprises an internal reflection parabolic mirror 7-2 with an intercept of 3<b<0.2 mm, a laser 1, and a compact Raman spectrometer; a parallel thin excitation beam is output from a single mode optical fiber 33 and a self-focusing lens 34, a SERS substrate 35 is applied on a cross-section of the internal reflection parabolic mirror 7-2, and remaining excitation beam 36 after excitation of the sample by total internal reflection is directed to a metal shell of the probe by the 45-degree long pass bichromal filter 37 with a hole in center of the filter and dissipates at the metal shell; a back-scattered Raman scattering beam of a sample is reflected by the parabolic mirror and is isolated from Rayleigh scattering by the 45-degree long pass bichromal filter 37 with a hole in center of the filter, and is focused by a lens 38 with a hole in a center of the lens, and is transferred to the Raman spectrometer via a multimode filter 39; and wherein an effective solid angle for collecting Raman scattering beam is 1.5-2πsr.

(7) The device for collecting the surface enhanced Raman scattering spectrum with a full aperture angle parabolic mirror may also be designed as a minimal invasive flexible or rigid surgery endoluminal smart parabolic Raman surgical knife; and a focal plane at an end of a compact truncated internal reflection parabolic mirror with an intercept of 3<b<0.2 mm is machined into a knife edge which cleaves at 30-60 degrees; while the knife edge cuts a tissue, Raman spectroscopy information on molecular vibration of the tissue is collected in real time at the knife edge of the parabolic mirror, determination is made on whether the cut tissue is a cancerous mass or other lesions or a normal tissue, 'positive/negative, +/−' information is seen or heard via a hardware and software system at instance according to Raman information base or comparison criteria of Raman information on cancer mass and non-cancerous tissue collected temporarily; the Raman surgical knife is connected to a compact laser and a compact Raman spectrometer via a flexible optical fiber or a rigid component for a parallel thin beam to construct a system of flexible or rigid surgery parabolic Raman smart surgical knife.

The excitation light source is a laser beam having a wavelength of near-infrared, or visible, or ultraviolet light; the external reflection parabolic mirror is made of hard copper, duralumin or titanium alloy, and is finely machined, and is plated or not plated reflection enhancing coating on a surface of the external reflection parabolic mirror; the internal reflection parabolic mirror is made of optical glass and optical quartz glass; the external reflection parabolic mirror or the internal reflection parabolic mirror is made of polymer optical organic polymer plastics and mold by a precise die, and is plated or not plated a transmission enhancing film or a reflection reducing film on a surface of the internal reflection parabolic mirror.

The sensitivity of Raman spectroscopy probe is the most important performance indicators. In case of the same slit, i.e., the same resolution, the key parameter to determine the sensitivity of the probe is the optical system transmission coefficient of the Raman scattering collecting system. In the case of the same brightness of the excitation light source on the surface of a sample and the same effective slit area A, ζ equals to the product of the aperture Ω of the collected Raman scattering and an area A', on the surface of the sample corresponding to the effective area A of the slit, i.e., ζ=Ω·A'. After roughly estimation, the ratio of the following Ω is as follows: wherein for a truncated parabolic Raman spectroscopy probe with Ω=2πsr; for a Raman spectroscopy probe available on the current market as a patent product with NA 0.25; and for a large Raman micro-spectrometer used for research with NA 0.5; the ratio of Ω is 2π:0.25:1; and ratio of three A'(ratio of focus square, such as the present invention parabolic mirror f=24 mm is designed, compared with other two f=12 mm and 4 mm) is about 4:1:1/9; the radio of three ζ is about 216:2:1. As such, the optical system transmission coefficient ζ of the parabolic mirror Raman spectroscopy probe is advantageous of two orders compared with the Raman spectroscopy probe with NA 0.25 available on the current market and the large scope Raman-spectrometer used for research.

The beneficial effects of the disclosure

A device for collecting surface-enhanced Raman spectrum with a full aperture angle parabolic mirror may be used for designing a new generation of compact, portable and hand-held Raman probe and spectrometer and flow particle Raman/micro-fluidic Raman analysis probe and Spectrometer, and may be widely used in cancer screening, disease diagnosis, food safety census, environmental testing and warfare agent detection and other trace analysis; a flexible or rigid endoluminal Raman spectroscopy probe and spectrometer and surgery Raman smart surgical knife will provide a new generation of convenient, accurate, and efficient instruments for minimal invasive endoluminal surgery. The device has a large market and is easy to use. The test concentration will meet the detection requirement in an order of μg-ng-fg/kg.

Figure 1:
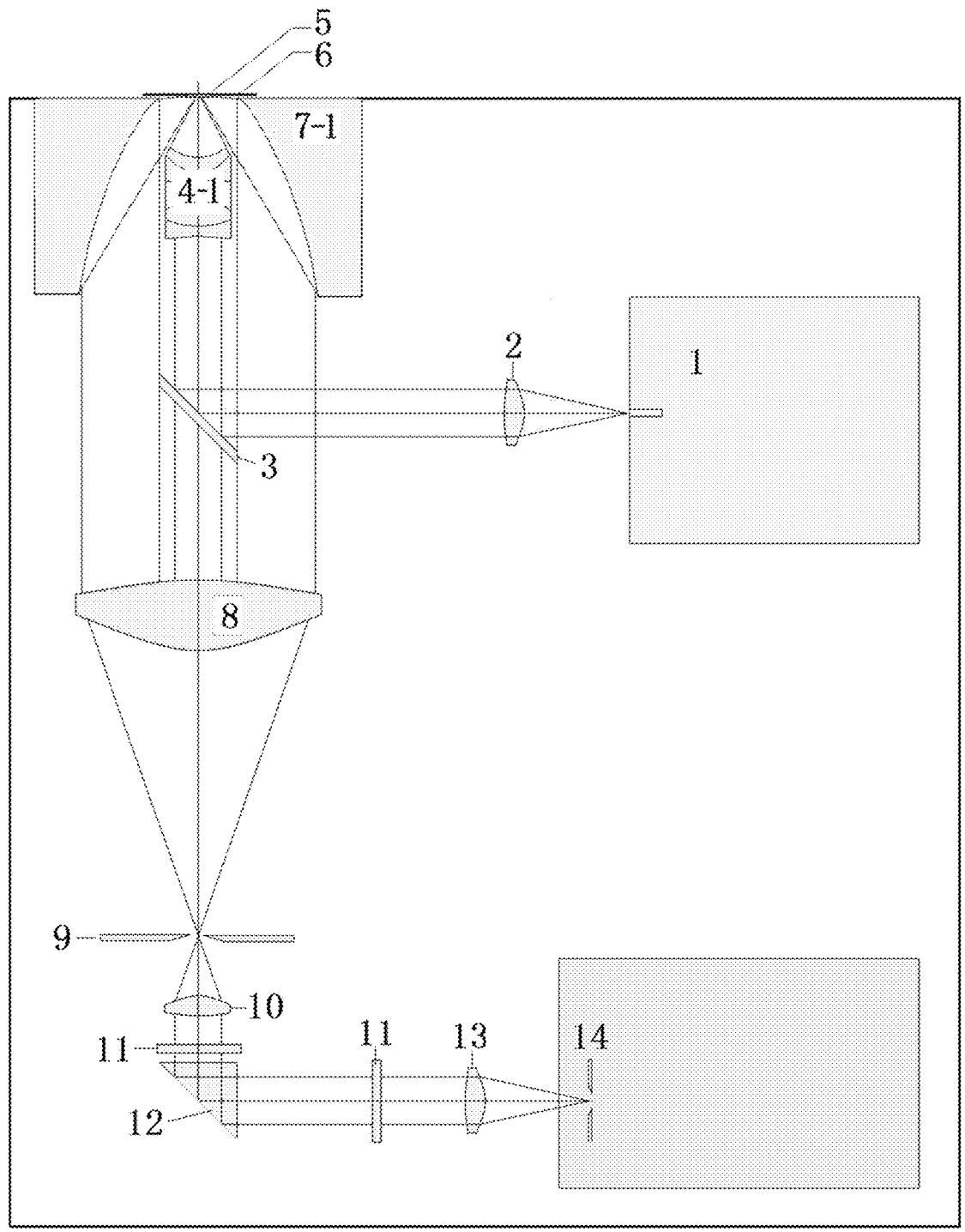
FIG. 1 is a schematic diagram of a portable, compact SERS device with a larger external reflection parabolic mirror.

In the drawings: 1 a laser; 2 a first lens; 3 a 45-degree incident long pass bichromal filter;

4-1 a built-in microscope objective; 4-2 an external microscope objective; 5 a SERS substrate+sample; 6 a slide;

7-1 an external reflection parabolic mirror; 7-2 an internal reflection parabolic mirror; 8 an aspheric large aperture objective lens; 9 a small spatial filter pinhole; 10 a small aperture lens; 11 a vertical incidence long-wavelength bichromal filter;

12 a total internal reflection prism or mirror or 45-degree short pass bichromal filter; 13 a second lens;

14 an optical fiber connector or compact spectrometer; 15 a third lens; 16 a linear micrometer, 17 a right angle prism; 18 a fourth lens; 19 a photodetector; 20 a hemispherical glass sample stage;

21 a wide-spectrum white light source; 22 an optical fiber spectrometer; 23 a hemispherical mirror with hemisphere surface having plated thereon short pass bichromal filtering film; 24 a capillary Raman sample cell;

26 an incident 45-degree short pass bichromal filter; 27 a sixth lens; 28 seventh lens; 29 an eighth lens; 30 a microspectrometer; 31 a housing of a hand-held compact parabolic SPR-SERS spectrometer; 32 a socket;

33 a single-mode optical fiber; 34 a self-focusing lens; 35 a SERS substrate;

36 remaining excitation beams after sample excitation via total internal reflection;

37 a 45-degree long pass bichromal filter with a hole in the center of the filter; 38 lens with a hole in the center of the lens;

39 a multi-mode optical fiber; 40 a housing of parabolic mirror surgical knife; b a parabolic mirror intercept; F-F a parabolic mirror focal plane; d-d trenches at end of an internal reflection parabolic mirror; 7-2-N a head of an internal reflection parabolic mirror Raman surgical knife;

7-2-N/X-X is a cross-sectional view of a surgical knife in a blade direction;

7-2-N/Y-Y is a sectional view of the surgical knife part in a direction perpendicular to a blade direction.

BEST EMBODIMENT OF THE DISCLOSURE

A schematic diagram of a portable large external reflection type parabolic mirror enhanced Raman spectroscopy probe and spectrometer with an intercept b=6 mm is shown in FIG. 1. The external reflection parabolic mirror 7-1 is made of hard copper and is finely machined by using diamond cutting tools on a precision computer numerical control (CNC) lathe. The probe and spectrometer is equipped with a single-mode polarization maintaining optical fiber which outputs a wavelength of 785 nm, a 40 mW semiconductor $TEM_{00}$ single-longitudinal-mode laser 1. The input of the single-mode polarization maintaining optical fiber is coupled to the focus of NA=0.2 lens 2 within the Raman spectroscopy probe, and then a parallel excitation beam is output. The parallel excitation beam is reflected by a band pass filter and a bichromal filter 3 which transmits a wavelength over 800 nm with 45 degree with respect to the main optical axis, and focused onto the focus of the external reflection parabolic mirror 7-1 by a microscope objective lens 4-1 with a long working distance NA0.5/40X provided on the main axis of the external reflection parabolic mirror 7-1. A SERS substrate+a sample 5 are provided on the focal plane. The beam greater than NA0.5 of the Raman beam back-scattered by the sample is reflected by the external refection parabolic mirror 7-1, and the beam less than NA0.5 of the Raman beam back-scattered by the sample is transmitted by the microscope objective mirror 4-1 with NA=0.5/40X. The parallel Raman scattering beam with large aperture is aggregated. The parallel beam is focused by an aspheric lens 8, is narrowed into a parallel beam with a small aperture by a pinhole 9 for blocking stray light, and is isolated from Rayleigh scattering by a long pass bichromal filter 11. The main optical axis is deflected by 90 degrees by a total internal reflection prism or mirror or 45-degree incident short pass bichromal filter 12. Then, the Raman beam is isolated from Rayleigh scattering and stray light by a long pass bichromal filter 11. The Raman beam is focused onto a optical fiber connector by a second lens 13, and is coupled to an incident slot of a compact optical fiber spectrometer via a multi-mode optical fiber to construct an enhanced Raman spectroscopy probe, or the focal spot of the Raman beam is adjusted onto a slot of a compact spectrometer to construct an integral compact enhanced Raman spectrometer.

DETAILED DESCRIPTION

Embodiments of the Present Disclosure

First Embodiment

Figure 2:
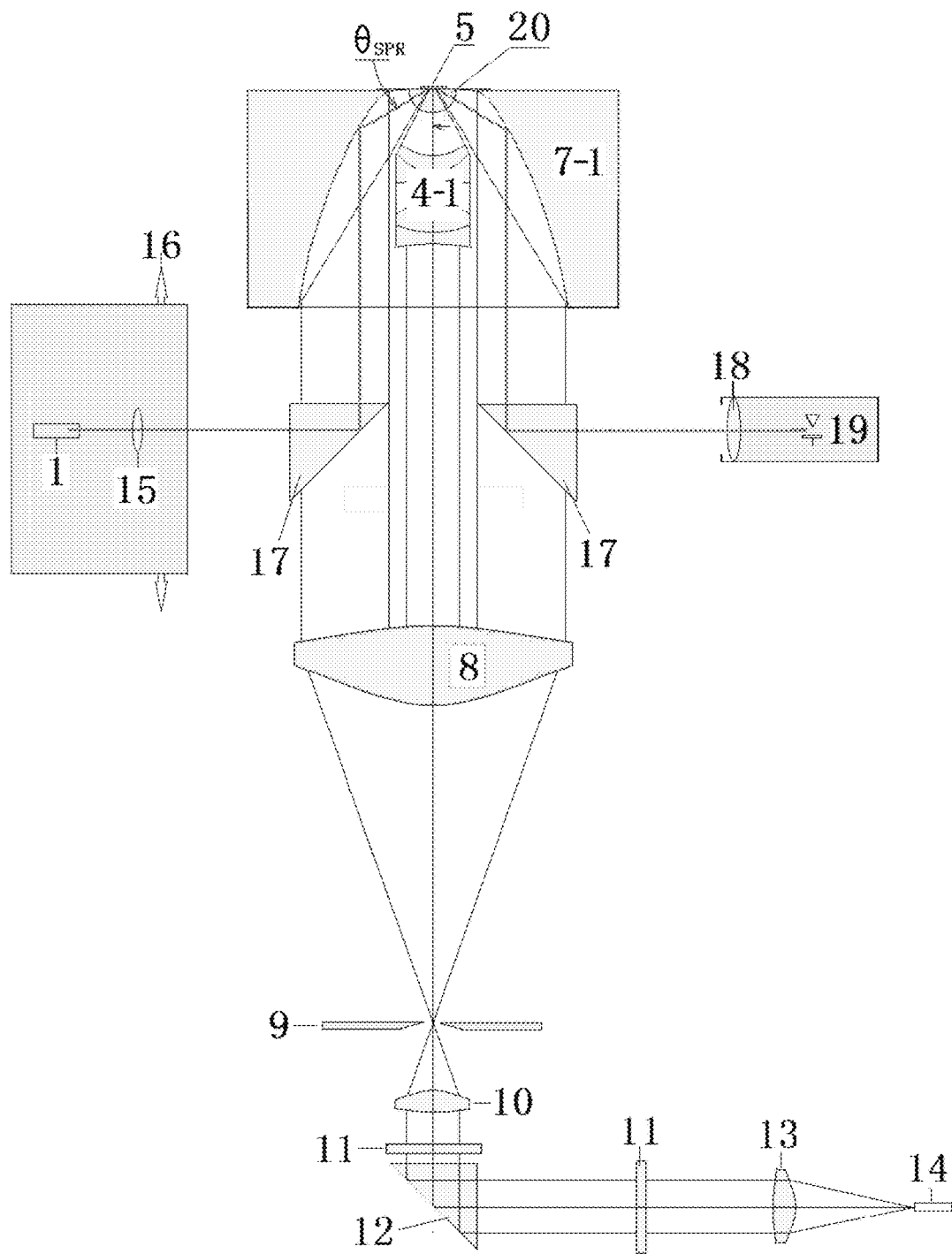
FIG. 2 is a schematic diagram of a portable SPR Raman spectroscopy device with a larger external reflection mirror.
Figure 3:
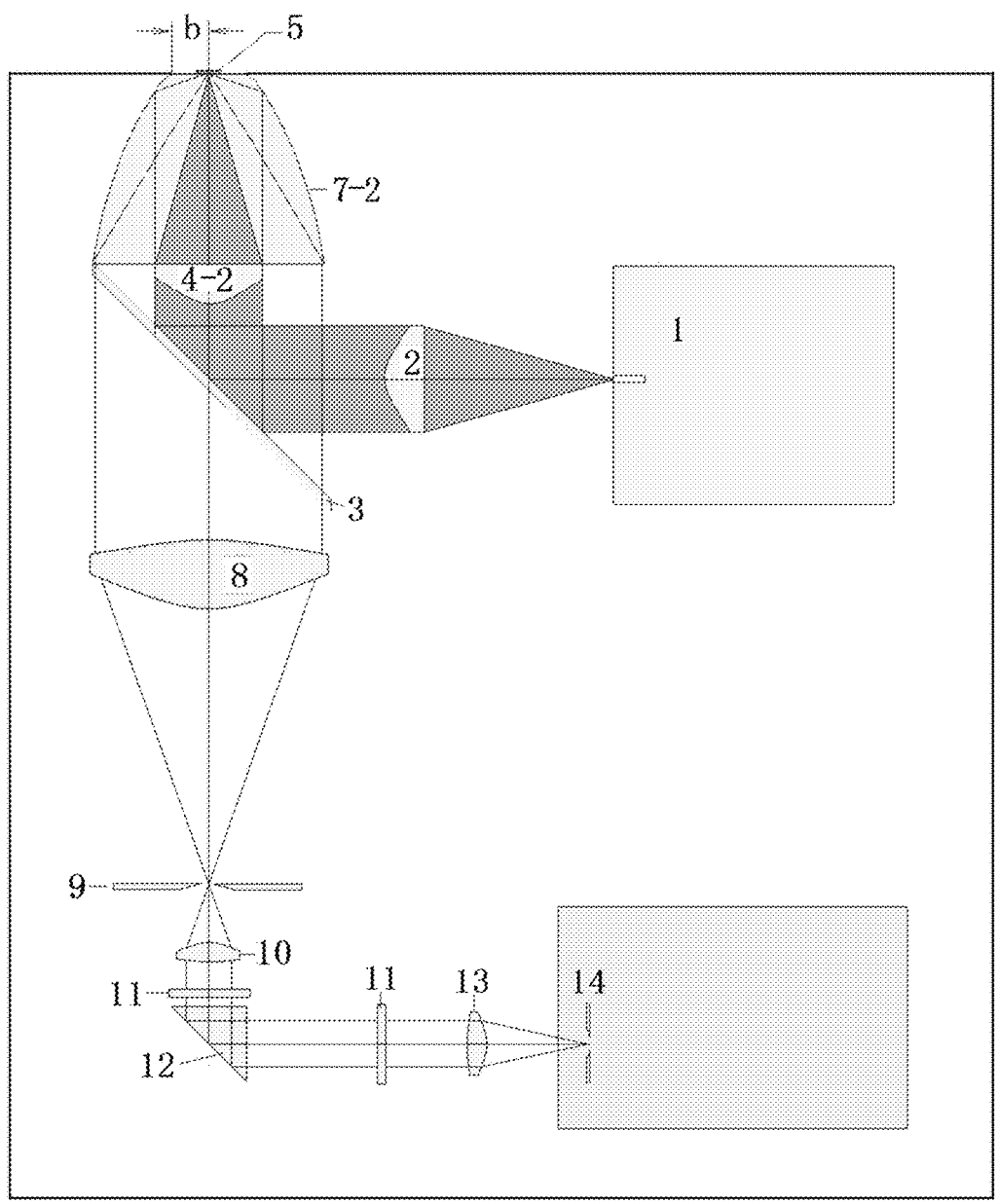
FIG. 3 is a schematic view of a portable SERS with larger internal reflection parabolic.

In the portable large external or internal reflection parabolic mirror Raman spectroscopy probe and spectrometer, a plug-in system for detecting the SPR Raman spectrum is added, so as to simultaneously detect the information on SPR Raman spectrum information and the refractive index n of the sample. As shown in FIG. 2, the SPR Raman spectroscopy plug-in system is placed in a large SPR Raman spectroscopy probe and spectrometer having an external reflection parabolic mirror with an intercept b=6 mm. The probe and spectrometer includes an excitation light source of 80 mW and 785 nm, a $TEM_{00}$ mode semiconductor laser 1 and a third lens 15. A parallel excitation beam is narrowed into a thin laser beam of 1 mm, or the semiconductor laser may be replaced with a compact solid laser with a parallel output aperture of about 1 mm. A linear straight-line trimmer 16 may be configured to adjust a thin laser beam to move up and down. The thin laser beam is deflected to be parallel with the main axis of the external reflection parabolic mirror by reflection using a small straight-angle prism 17 with thickness of 4 mm, and is reflected by the parabolic mirror and then is focused onto a SERS substrate+a sample 5 on a hemispherical quartz optical glass sample stage 20 the center of which overlaps with the focus of the external reflection parabolic mirror 7-1. The Raman scattering beam is totally internally reflected by the sample and is deflected onto "a fourth lens 18+a photo-detector 19" by a second straight-angle prism 17 with thickness of 4 mm. The linear straight-line trimmer 16 may be configured to adjust the assembly of "an excitation light source+a third lens 15" to adjust an incident angle of the beam with respect to the sample. When the signal of the photo-detector 19 has a minimum value, the incident angle is adjusted to $\theta_{SPR}$, such that the excitation beam performs coupling resonance with respect to the SERS substrate+the sample 5. As such, a parallel Raman scattering beam with a large aperture collected by the external reflection parabolic mirror 7-1 and the build-in microscope objective lens 4-1 passes through an aspherical objective lens 8 with a large aperture and the same subsequent Raman optical system as that shown in FIG. 1, and then SPR Raman scattering spectrum of the sample may be detected. Before SPR Raman scattering spectrum of the sample is detected, a sample n with a known reflective efficient, for example, pure water or other sample with a known reflective efficient may be used, and a standard curve n-$\theta_{SPR}$ of relationship between a reflective efficient n of a sample and readings of the linear straight-line trimmer 16 corresponding to the incident angle $\theta_{SPR}$ for the instrument is calibrated according to the relationship between readings of the linear straight-line trimmer 16 and the incident angel $\theta_{SPR}$. Based on the standard curve of the instrument, SPR Raman spectrum of the sample may be detected while data of a reflective efficient of an unknown sample is detected.

Second Embodiment

Figure 4:
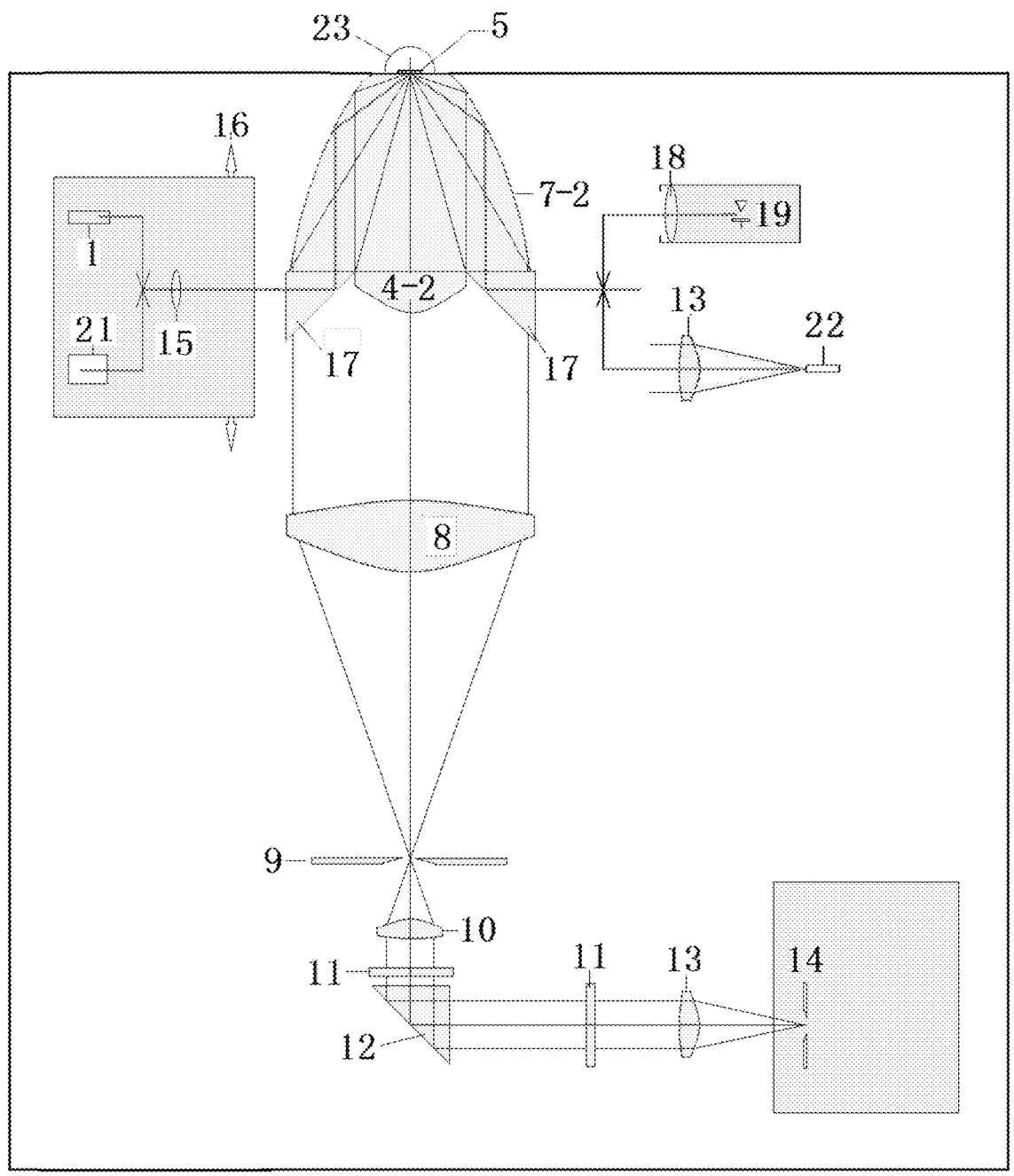
FIG. 4 is a schematic diagram of a SPR-internal reflection larger parabolic mirror portable compact Raman/dual absorption spectrums and refractive index triple-function spectrum analyzer.

In the above-mentioned portable parabolic mirror large SPR Raman spectrum enhanced probe with an external reflection parabolic mirror or an internal reflection parabolic mirror, a plug-in system for detecting absorption spectrum of a sample. As shown in FIG. 4, in the SPR Raman spectrum enhanced probe and spectrometer having an internal reflection parabolic mirror with an intercept of b=6 mm, the plug-in system for detecting absorption spectrum of a sample includes an assembly of a wide spectrum white light source and an assembly of "a fifth lens 13+an optical fiber spectrometer 22". After adjusting and detecting SPR Raman spectrum and reflective efficient of the sample, a laser 1 for exciting SPR Raman spectrum is replaced with the wide spectrum white light source, and an assembly of "a fourth lens 18+a photo-detector 19" is replaced with the assembly of "the fifth lens 13+the optical fiber spectrometer 22", such that transmission efficient of the sample may be detected. As such, a SPR spectrum analysis device having SPR Raman/double absorption spectrums and reflective efficient triple-function may be achieved.

Third Embodiment

Figure 5:
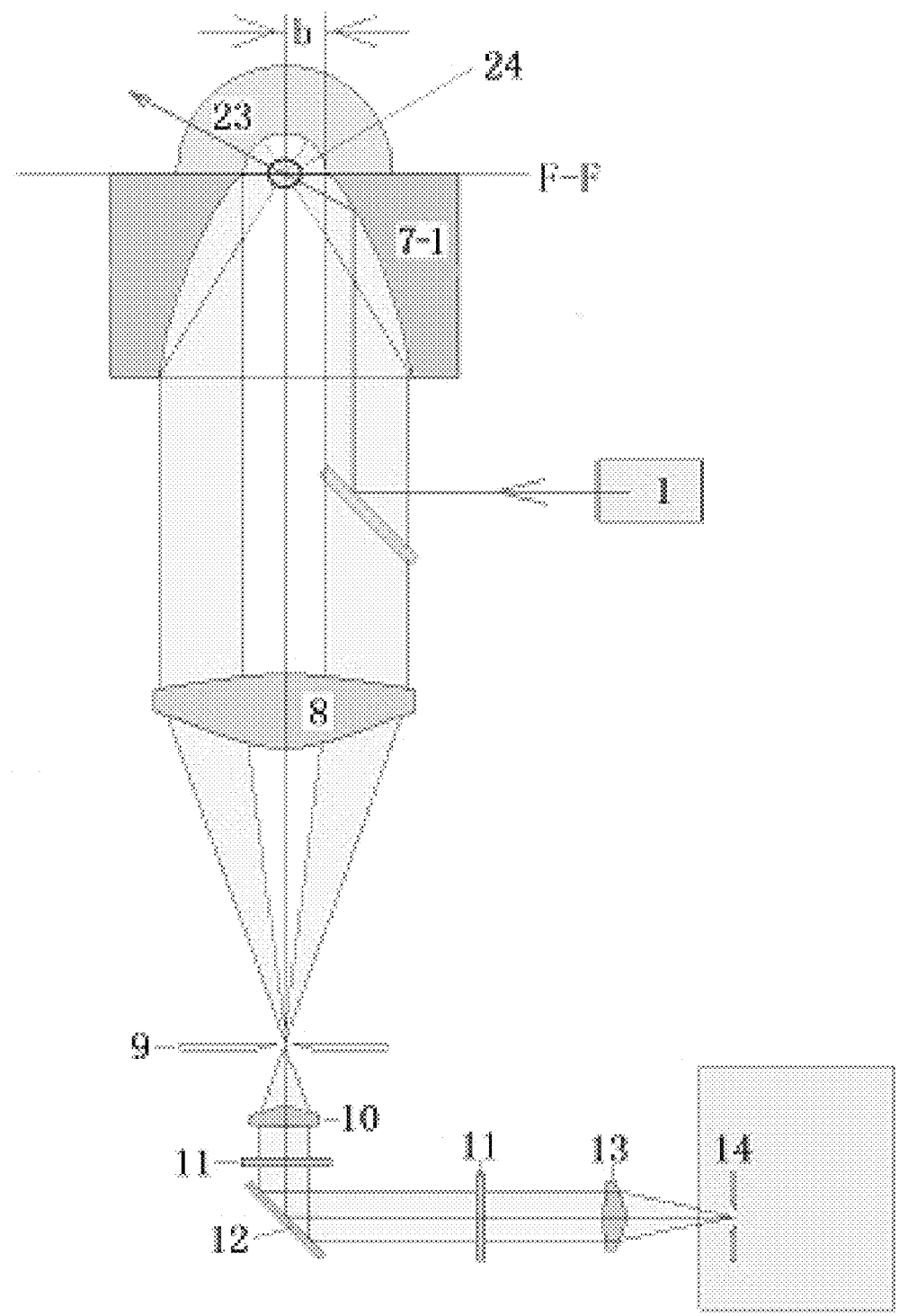
FIG. 5 is a schematic diagram of a probe and spectrometer of near ultraviolet (UV)optical flow type particle Raman analysis/micro-fluidic Raman analysis.

The device for collecting surface enhanced Raman scattering spectrum with a full aperture angle parabolic mirror may be designed as a flow particle Raman analysis/micro-fluidic Raman analysis probe and spectrometer. The probe and spectrometer includes a "back" scattering type of $2\pi$ flow particle Raman analysis/micro-fluidic Raman analysis probe and spectrometer and a "back+forward" scattering type of $4\pi$ flow particle Raman analysis/micro-fluidic Raman analysis probe and spectrometer. FIG. 5 shows a specific example of a parabolic mirror flow particle Raman analysis with near ultraviolet excitation/micro-fluidic Raman analysis probe. A mirror 23 having plated a short pass bichromal filtering film on a surface of the hemisphere and having a center overlapping the focus of the parabolic is provided on the cross section of the external reflection parabolic mirror 7-1. The axis of a quartz glass capillary Raman sample cell 24 passes through the focus of the parabolic mirror. For ensuring the transmission efficient of the whole system for near ultraviolet, the whole system including the Raman spectrometer needs reflection parts or quartz transmission parts, and will not use optical fiber to connect the probe with the laser and spectrometer. Near ultraviolet laser 1 may adopt a 355 nm wavelength solid laser with 3 frequency multiplying for 1064 nm wavelength. A parallel thin laser beam directly passes through a mirror having plated thereon transmission film and an external reflection parabolic mirror 7-1, and is focused onto a sample in a quartz capillary Raman sample cell 24 provided on the focus of the parabolic mirror. For purpose of improving a signal-noise-ratio of Raman scattering beam of the sample, the forward laser beam remained after exciting the sample to generate Raman scattering and after loss passes through the mirror 23 having plated a short pass bichromal filtering film on a surface of hemisphere, and a Raman probe is extended. The $4\pi sr$ Raman scattering beam of the sample has a collection blind zone of 2sr in the system of "an external reflection parabolic mirror 7-1 with an intercept of b=6 mm+a mirror 23 having plated short pass bichromal filtering film on a surface of hemisphere". Thus, the aperture angle of the ultraviolet light excitation flow particle Raman analysis/micro-fluidic Raman analysis probe and spectrometer for collecting Raman scattering beam is about 10sr.

Fourth Embodiment

Figure 6:
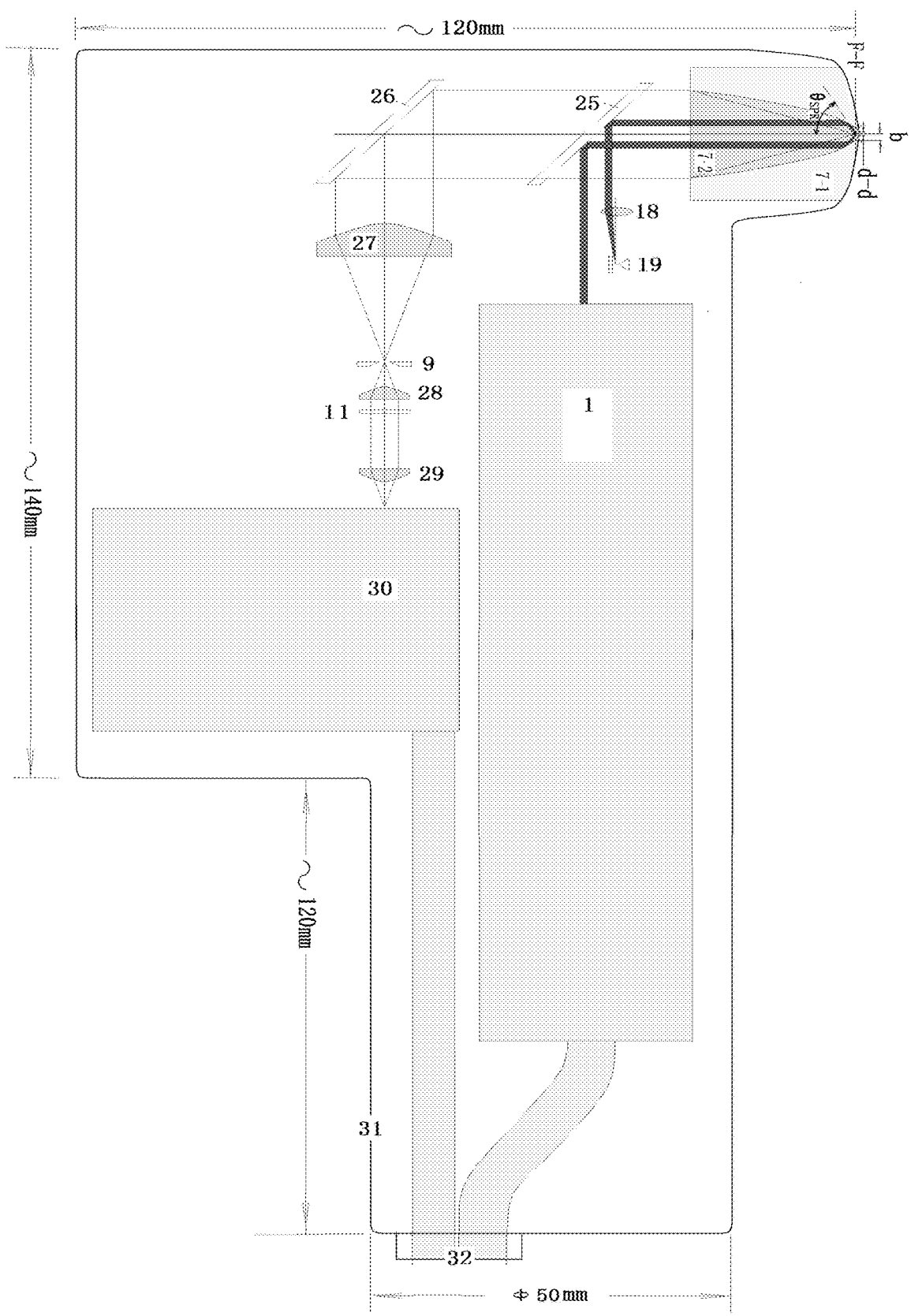
FIG. 6 is schematic diagram of a hand-held compact parabolic SPR-SERS Raman spectrometer.

The device for collecting surface enhanced Raman scattering spectrum with a full aperture angle parabolic mirror may also be designed as a hand-held compact SPR-SERS Raman spectrometer with ultrahigh sensitivity. It adopts a compact external reflection parabolic mirror or a compact internal reflection parabolic mirror with an intercept of 3<b<0.2 mm, including two types, i.e., a type of a truncated parabolic mirror and a type of a whole parabolic mirror. As shown in FIG. 6, a compact parabolic mirror has an intercept of b=1 mm. There are provided a housing 31 of a hand-held SPR-Raman spectrometer and a power source 32. In the hand-held compact parabolic mirror SPR-SERS Raman spectrometer, a hole or trench matching a capillary sample cell extends from the top to the focus of the end of the whole compact parabolic mirror. The sample is sucked into the capillary SERS Raman chip. The SERS substrate in the capillary is located at the focus. The SPR Raman spectrum of the sample is detected. The aperture for collecting the Raman scattering beam may be up to 3-4πsr. FIG. 6 shows an estimation of shape and size of a compact parabolic mirror hand-held SPR-SERS Raman spectrometer. As shown in FIG. 5, it is assumed that a homebred single longitudinal mode He—Ne laser with a wavelength 632.8 nm, 1.5 mW, $TEM_{00}$, line polarization 500:1 and good coherence, the hand-held compact Raman spectrometer has a length of about 260 mm, wherein the handle has a length of 600 mm and a diameter of 50 mm. It is assumed that a homebred single longitudinal mode solid laser with a wavelength 532 nm, 50 mW, $TEM_{00}$, line polarization 100:1 and good coherence, the hand-held compact Raman spectrometer has a length of about 180 mm, wherein the handle has a length of 60 mm.

Fifth Embodiment

Figure 7:
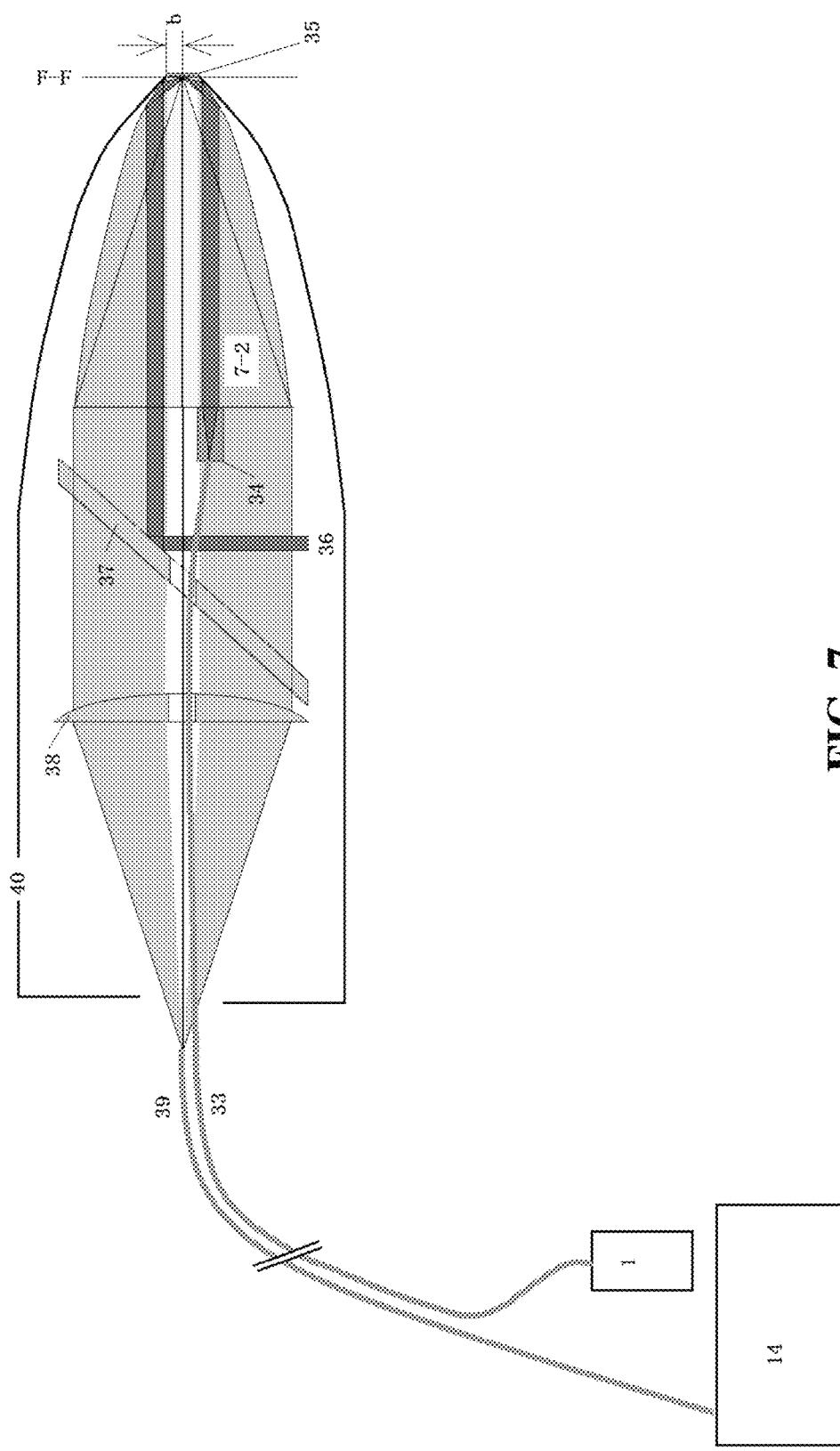
FIG. 7 is a schematic diagram of a hand-held flexible compact parabolic Raman spectrometer for surgical procedures.
Figure 8:
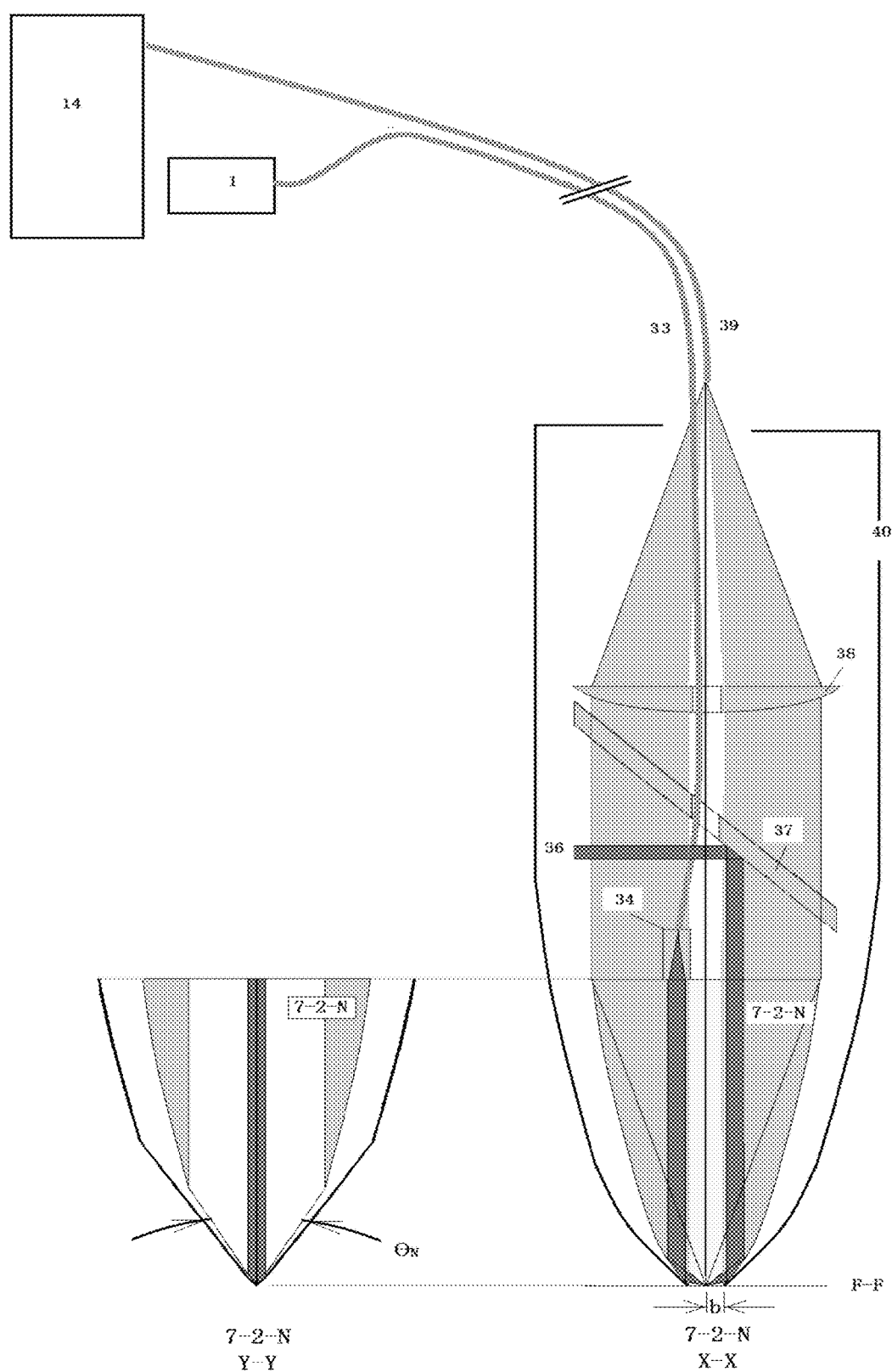
FIG. 8 is schematic diagram of a hand-held flexible compact surgical parabolic Raman smart knife.

The device for collecting surface enhanced Raman scattering spectrum with a full aperture parabolic mirror may be designed as minimal invasive flexible or rigid endoluminal Raman spectroscopy probe and spectrometer. A compact parabolic object of quartz may be used, with an intercept of 3>b>0.2 mm. The rigid minimal invasive endoluminal Raman spectrometer adopts conventional lens structure to transmit a parallel excitation beam and Raman scattering beam of a sample. The flexible minimal invasive endoluminal Raman spectrometer adopts optical fiber enclosed in a flexible tube to transmit the two beams. FIG. 7 shows a divided structure in which a flexible optical fiber connects the Raman probe and a laser and spectrometer. When an internal reflection parabolic mirror Raman probe made of quartz and with an intercept of b=0.2 mm, the parabolic mirror has an outer diameter of 3 mm, a length of 15 mm, and the metal housing of the probe is about 5 mm with a length of about 15 mm. The probe is connected with a $TEM_{00}$ single longitudinal mode laser 1 via a single mode optical fiber 33, and is connected with a compact spectrometer 14 via a multi-mode optical fiber 39. The single mode optical fiber 33 within the probe is coupled to a parallel thin excitation beam output from a focusing lens 34. The thin excitation beam then is reflected and focused onto the sample on the SERS substrate 35 on the focal plane F-F by the internal parabolic mirror 7-2. The excitation beam 36 remained after total internal reflection of the sample and excitation of the sample is reflected by a 45-degree long pass bichromal filter 37 with a hole in its center, and directed to be dissipated at the metal housing of the probe. The Raman scattering beam of the sample is focused by a ninth lens 38 with a hole in its center, and is transmitted to a compact spectrometer for isolating Rayleigh scattering by a coupled multi-mode optical fiber. The effective solid angle for collecting Raman scattering beam is approximate to 2πsr.

Sixth Embodiment

In the device for collecting surface enhanced Raman scattering spectrum with a full aperture angle parabolic mirror, on the basis of the minimal invasive endoluminal Raman spectroscopy probe and spectrometer, the Raman probe is modified into a minimal invasive surgery parabolic mirror Raman smart surgical knife. A surgery smart surgical knife is machined at the front end of the compact internal reflection parabolic mirror with an intercept of 0.2<b<3 mm. The end of the internal reflection parabolic mirror made of quartz or gemstone is machined into a cleave with an angle of 30-60 degrees. The cross-section of the internal reflection parabolic mirror is machined into a knife edge, the middle of which is sensitive region for Raman detection. The solid angle of effectively collecting Raman spectrum of the Raman optical system is approximate to last While the parabolic mirror Raman smart surgical knife is performing a surgery and cutting, determination may be made on whether the cut portion is a cancer mass or not by the hand-held Raman surgical knife.

INDUSTRIAL APPLICABILITY

A device for collecting surface-enhanced Raman spectrum with a full aperture angle parabolic mirror may be used for designing a new generation of compact, portable and hand-held Raman probe and spectrometer and flow particle Raman/micro-fluidic Raman analysis probe and Spectrometer, and may be widely used in cancer screening, disease diagnosis, food safety census, environmental testing and warfare agent detection and other trace analysis; a flexible, rigid endoluminal Raman spectroscopy probe and spectrometer and surgery Raman smart surgical knife will provide a new generation of convenient, accurate, and efficient instruments for minimal invasive endoluminal surgery. The device has a large market and is easy to use. The test concentration will meet the detection requirement in an order of μg-ng-fg/kg.

I claim:

1. A device for collecting surface-enhanced Raman spectrum by a full aperture angle parabolic mirror, wherein the device is a SERS probe and spectrometer, a surface plasmon resonance SPR Raman spectroscopy probe and spectrometer, a SPR Raman/absorption dual-spectrum and refractive index triple-function probe and spectrometer, a flow particle Raman analysis/micro-fluidic Raman analysis probe and spectrometer, a minimal invasive flexible endoluminal Raman spectroscopy probe and spectrometer, or a surgery Raman intelligent surgical knife; an enhanced Raman probe in each of the above six devices is equipped with a good coherence compact $TEM_{00}$ single longitudinal mode laser and a compact spectrometer, the $TEM_{00}$ single longitudinal mode laser using single-mode fiber and the compact spectrometer using multi-mode fiber, the good coherence compact $TEM_{00}$ single longitudinal mode laser and the compact spectrometer are connected by an optical fiber to the Raman spectroscopy probe, or the laser and the compact spectrometer as well as an optical path of the Raman spectroscopy probe are designed as an integrated compact Raman spectrometer; wherein the full aperture angle of the device for collecting surface enhanced Raman spectrum is 1.5-2πsr or 3.5-4πsr.

2. The device according to claim 1, wherein the SERS probe and spectrometer comprises a single mode optical fiber connector or laser (1), a first lens (2), a 45-degree incident long pass bichromal filter (3), a SERS substrate+sample (5), a slide (6), an external reflection parabolic mirror (7-1) equipped with a coaxial confocal built-in microscope objective lens (4-1), an internal reflection parabolic mirror (7-2) equipped with a coaxial confocal external microscope objective lens (4-2), an aspherical large aperture objective lens (8), a small space filter pinhole (9), a small aperture lens (10), a vertically incident long pass bichromal filter (11), a total internal reflection prism or mirror or 45-degree short pass bichromal filter (12), a second lens (13) and an optical fiber connector or a compact spectrometer (14);

wherein through the single-mode fiber connector or laser (1), a laser beam with good coherence is converted into a parallel excitation laser beam by the first lens (2), and passes through a 45-degree incident long pass bichromal filter (3) provided on a main optical axis; then the optical path is branched into a first structures using the external reflection parabolic mirror (7-1) or the second structure using the internal reflection parabolic mirror (7-2), wherein in the first structure using the external reflection parabolic mirror, the excitation laser beam passes through the built-in microscope objective lens (4-1), and in the second structure using the internal reflection parabolic mirror, the excitation laser beam passes through the external microscope objective lens (4-2); the excitation laser beams for the two structures are both focused onto the SERS substrate+sample (5) provided on the slide (6), and the SERS Raman scattering beam in about 2π solid angle as back-scattered by the sample passed through the two above structures objectives and reflected by parabolic mirrors, and is collected and synthesized into a large aperture parallel beam, the large aperture parallel beam is focused by the aspherical surface large aperture lens (8), and is isolated from stray light via the small space filtering pinhole (9), then is converted into a small aperture parallel beam by the small aperture lens (10) and is isolated from Rayleigh scattering by the long pass bichromal filter (11), the main optical axis is deflected by 90 degrees by the total internal reflection prism or mirror or 45-degree incident short pass bichromal filter (12), and the small aperture parallel beam is isolated from Rayleigh scattering and stray light by the long pass bichromal filter (11), and Raman beam is focused onto the optical fiber connector by the second lens (13) and is coupled onto an incident slit of a compact optical fiber spectrometer by a multi-mode optical fiber to construct a compact SERS probe, or the focal spot of the Raman beam is adjusted directly onto a slit of a compact spectrometer to construct a compact SERS spectrometer;

wherein the intercept of the external reflection parabolic mirror (7-1) and the internal reflection parabolic mirror (7-2), both truncated at a focus, the intercept b is about 4 to 10 mm, and the parallel output backscattered Raman scattering beam collected by the reflection of each mirror is a hollow parallel beam, in the hollow blind zone respectively designed and provided with a built-in microscope objective (4-1) with a long working distance and a numerical aperture NA=0.4-0.5 for external reflection parabolic mirror 7-1, and for the internal reflection parabolic mirror 7-2 provided with an external microscope objective lens (4-2) with NA of 0.25; on the one hand to ensure good coherence of the excitation beam and spot size of 2-10 μm focused on the sample, so that SERS of sample has ultra-high enhancement factor; on the other hand to use the built-in microscope objective lens (4-1) and the external microscope objective lens (4-2) such that Raman beams in the reflection blind zone of the external reflection parabolic mirror (7-1) and the internal reflection parabolic mirror (7-2) are collected, so that a total effective full aperture angle of backscattered Raman scattering beam achieved of 1.8-2πsr.

3. The device according to claim 2, wherein in the SERS probe and spectrometer, two systems of reflection parabolic mirror, i.e., a system using an external reflection parabolic mirror or a system using an internal reflection parabolic mirror are used, a plug-in system is additionally provided for detecting SPR Raman spectrum to construct a SPR Raman spectroscopy probe and spectrometer,the plug-in system comprises a laser (1), a build-in microscope objective (4-1) corresponding to an external reflection parabolic mirror (7-1), or an external microscope objective (4-2) corresponding to an internal reflection parabolic mirror (7-2),a third lens 15, a linear straight-line trimmer (16), a right-angle prism (17), the fourth lens (18), a photoelectric detector (19) and a hemispherical glass sample stage (20); an excitation beam generated by the laser (1) is narrowed by the third lens (15) to reduce the diameter of the excitation beam to 1-2 mm thin laser beam, the thin laser beam is deflected by a right-angle prism (17) with a thickness of 3-4 mm to be parallel to the main optical axis and then reflected by the external reflection parabolic mirror (7-1) or the internal reflection parabolic mirror (7-2) to be focused on a focus of the corresponding parabolic mirror, wherein in case of the external reflection parabolic mirror (7-1),a hemispherical quartz glass sample stage (20)is provided; the laser beam totally internally reflected by the SERS substrate+sample (5) is reflected by the external reflection parabolic mirror (7-1) or the internal reflection parabolic mirror (7-2) and deflected onto a fourth lens (18) by a second right-angle prism (17) with a thickness of 3-4 mm and then directly enters the photoelectric detector system (19); the 'laser (1)+the third lens (15)' is adjusted by the linear micrometer (16) to achieve micro displacement in a direction parallel to the main optical axis, that is, an incident angle of an excitation beam with respect to the 'SERS substrate+sample (5)' is adjusted; the incident angle is adjusted to the SPR incident angle $\theta_{SPR}$ such that the excitation beam is coupled to and resonates with the SPR of 'SERS substrate+sample (5)'; while adjusting the incident angle of the excitation laser beam by the linear micrometer (16), the intensity of the SPR reflected beam is read and detected by the photoelectric detector (19), and when the photoelectric detector (19) shows a minimum value, the incident angle reaches the SPR-$\theta_{SPR}$; at this time, the detected Raman spectrum is the SPR Raman spectrum of the sample; and an unknown refractive index n of the sample is detected according to readings of the linear micrometer (16) and a standard curve n-$\theta_{SPR}$ calibrated using a refractive index of a known sample, such as pure water and other pure liquids.

4. The device according to claim 3, wherein instead of the linear micrometer (16) which adjusts the position of 'the laser (1)+the third lens (15)', a precise optical flat glass is inserted into a parallel thin laser beam generated by the laser (1) in a SPR Raman spectroscopy probe and spectrometer, the optical flat glass is fixed on stage with a precise electric control detecting angular displacement to control and measure a rotary angle of the optical flat glass, and the rotary angle of the optical flat glass adjusts translational movement of the parallel thin laser beam, such that an incidence angle $\theta_{SPR}$ of the excitation beam with respect to SERS substrate+sample (5) is adjusted.

5. The device according to claim 3, wherein a plug-in system for detecting absorption spectrum of a sample is added to the SPR Raman spectroscopy probe and spectrometer, and the plug-in system comprises an assembly of 'a wide-spectrum white light source(21) and a fifth lens (13)+ optical fiber spectrometer (22)' to construct a SPR Raman/absorption dual spectrums and refractive index three-function Raman probe and spectrometer; the plug-in system for detecting SPR Raman spectrum is adjusted to make the incident angle of the excitation beam to locate at SPR-$\theta_{SPR}$, SPR-Raman spectrum detection and refractive index detection of the SERS substrate+sample (5) are performed; then, a switching to the plug-in system assembly for detecting absorbtion spectrum of the sample is performed: the laser (1) for exciting the SPR Raman spectrum is replaced with the wide-spectrum white light source (21), an assembly of 'a fourth lens (18)+a photoelectric detector (19)' is replaced with an assembly of 'a fifth lens (13)+an optical fiber spectrometer (22)', to detect the absorption spectrum of the same sample, to achieve the SPR Raman/absorption dual spectrums and refractive index three-function spectrum analysis of the sample.

6. The device according to claim 1, wherein the device for collecting the surface enhanced Raman scattering spectrum with a full aperture angle parabolic mirror is designed as a flow particle Raman analysis/micro-fluidic Raman analysis probe and spectrometer, comprising a 'back' scattering type and a 'back+forward' scattering type two types of flow particle Raman analysis/micro-fluidic Raman probe and spectrometer, is divided into non-truncated monolithic internal parabolic mirror system and focal plane F-F truncated external reflection parabolic mirror system; a monolithic internal parabolic mirror system, wherein a hole or groove d-d matching an outer diameter of a capillary sample cell extends from a top to a focus of the internal parabolic mirror, the hole being perpendicular to the main optical axis; and a focal plane F-F truncated external reflection parabolic mirror system, wherein a mirror (23) with a hemisphere surface having plated thereon a short pass bichromal filtering film is provided on a focus plane of the external reflection parabolic mirror, a spheroid center of the mirror is overlapped with a focal point of the external reflection parabolic mirror;

the focal plane F-F truncated external reflection parabolic mirror system is applied to a near UV excitation Raman spectroscopy system, the whole system uses reflective components and quartz transmission components; thin parallel near ultraviolet laser beam emitted by an near ultraviolet laser (1) is reflected by a 45-degree mirror and is reflected by an external reflection parabolic mirror (7-1) and focused onto a capillary Raman sample cell (24), axis of which passes through a focus of the parabolic mirror; an intercept b of the parabolic mirror is 3-6 mm, and an effective aperture angle of the system of 'hemispherical mirror+the external reflection parabolic mirror' for collecting Raman scattering beam is 3.5-4$\pi$sr.

7. The device according to claim 1, wherein the SERS probe and spectrometer is designed as a hand-held SPR Raman spectrometer and comprises a laser (1), an external reflection parabolic mirror (7-1) or an internal reflection parabolic mirror (7-2), a small space filtering pinhole (9), an incident 45-degree long pass bichromal filter (25), an incident 45-degree short pass bichromal filter (26), a sixth lens (27), a seventh lens (28), an eighth lens (29) and a microspectrometer; the hand-held SPR Raman spectrometer is divided into two types, i.e., a type of a truncated parabolic mirror and a type of a whole parabolic mirror, an intercept of the parabolic mirror 3<b<0.2 mm, a hole or groove d-d perpendicular to the main optical axis extends from a top to a focus of the whole parabolic mirror and is configured to receive the capillary sample cell or micro-channel Raman chip, an effective aperture angle of the Raman optical system for collecting Raman scattering is 3.5-4$\pi$sr.

8. The device according to claim 1, wherein the SERS probe and spectrometer is designed as a minimal invasive flexible endoluminal Raman spectroscopy probe and spectrometer, the minimal invasive flexible endoluminal Raman spectroscopy probe and spectrometer uses a flexible optical fiber to connect the probe to a laser and the spectrometer, and comprises an internal reflection parabolic mirror (7-2) with an intercept of 3>b>0.2 mm, a laser (1), and a compact Raman spectrometer; a parallel thin excitation beam is output from a single mode optical fiber (33) and a self-focusing lens (34), a SERS substrate (35) is applied on a cross-section of the internal reflection parabolic mirror (7-2), and remaining excitation beam(36) after excitation of the sample by total internal reflection is directed to a metal shell of the probe by the 45-degree long pass bichromal filter (37) with a hole in center of the filter and dissipates at the metal shell; a back-scattered Raman scattering beam of a sample is reflected by the parabolic mirror and is isolated from Rayleigh scattering by the 45-degree long pass bichromal filter (37) with a hole in center of the filter, and is focused by a lens (38) with a hole in a center of the lens, and is transferred to the Raman spectrometer via a multimode filter (39); and wherein an effective solid angle for collecting Raman scattering beam is 1.5-2$\pi$sr.

9. The device according to claim 1, wherein the SERS probe and spectrometer is designed as minimal invasive flexible or rigid endoluminal surgery parabolic smart Raman surgical knife; and a focal plane at an end of a compact truncated internal reflection parabolic mirror with an intercept of 3<b<0.2 mm is machined into a knife edge which cleaves at 30-60 degrees; while the knife edge cuts a tissue, Raman spectroscopy information on molecular vibration of the tissue is collected in real time at the knife edge of the parabolic mirror, determination is made on whether the cut tissue is a cancerous mass or other lesions or a normal tissue, 'positive/negative, (+)/(−)' information is seen or heard via a hardware and software system at instance according to Raman information base or comparison criteria of Raman information on cancer mass and non-cancerous tissue collected temporarily; the Raman surgical knife is connected to a compact laser and a compact Raman spectrometer via a flexible optical fiber or a rigid component for a parallel thin beam to construct a system of flexible or rigid surgery parabolic Raman smart surgical knife.

10. The device according to claim 1, wherein the excitation light source is a laser beam having a wavelength of near-infrared, or visible, or ultraviolet light; the external reflection parabolic mirror is made of hard copper, duralumin or titanium alloy, and is finely machined, and is plated or not plated reflection enhancing coating on a surface of the external reflection parabolic mirror; the internal reflection parabolic mirror is made of optical glass and optical quartz glass; the external reflection parabolic mirror or the internal reflection parabolic mirror is made of polymer optical organic polymer plastics and mold by a precise die, and is plated or not plated a transmission enhancing film or a reflection reducing film on a surface of the internal reflection parabolic mirror.

11. The device according to claim 1, wherein on the sample stage of the device is installed with or without a hemisphere mirror (23), on the hemisphere surface having plated short pass bichromal filter film, the center of hemisphere mirror (23) is homocentric with respect to a focal point of the parabolic mirror, and the aperture angle of the Raman optical system for collecting the Raman scattered beam is 3.5-4πsr or 1.8-2πsr.

12. The device according to claim 1, a method of sensitivity calculating and parameters designing of collecting surface-enhanced Raman spectrum with full aperture angle parabolic mirror is provided, wherein the primary parameter to determine the sensitivity of the probe is the optical system transmission coefficient ζ of the Raman scattering collecting system, in the case of the same brightness of the excitation light source on the surface of a sample and the same effective slit area A, ζ equals to the product of the aperture angle Ω of the collected Raman scattering and an area A' on the surface of the sample corresponding to the effective area A of the slit, i.e., ζ=Ω·A'; after calculation, the ratio of the following Ω is as follows: wherein for a truncated parabolic Raman spectroscopy probe with Ω=2πsr; for a Raman spectroscopy probe available on the current market as a patent product with NA 0.25; and for a large Raman microspectrometer used for research with NA 0.5; the ratio of Ω is 2π:0.25:1; and ratio of the three A' (ratio of focus square, such as parabolic mirror f=24 mm is designed, compared with other two f=12 mm and 4 mm) is 4:1:1/9; the radio of the three ζ is about 216:2:1; as such, the optical system transmission coefficient of the parabolic mirror Raman spectroscopy probe the present application provided is advantageous of two orders compared with the Raman spectroscopy probe with NA 0.25 available on the current market and the large scope Raman-spectrometer used for research.

* * * * *